(12) United States Patent
Graboi et al.

(10) Patent No.: US 8,113,062 B2
(45) Date of Patent: Feb. 14, 2012

(54) TILT SENSOR FOR USE WITH PROXIMAL FLOW SENSING DEVICE

(75) Inventors: Daniel G. Graboi, Encinitas, CA (US); Chester Hinson, Oceanside, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 93 days.

(21) Appl. No.: 12/570,956

(22) Filed: Sep. 30, 2009

(65) Prior Publication Data

US 2010/0077866 A1    Apr. 1, 2010

Related U.S. Application Data

(62) Division of application No. 61/101,190, filed on Sep. 30, 2008.

(51) Int. Cl.
*G01F 1/00* (2006.01)
(52) U.S. Cl. ........................................................ 73/861
(58) Field of Classification Search .................. 600/486; 73/861
See application file for complete search history.

(56) References Cited

U.S. PATENT DOCUMENTS

| | | |
|---|---|---|
| 5,038,621 A | 8/1991 | Stupecky |
| 5,146,092 A | 9/1992 | Apperson et al. |
| 5,153,436 A | 10/1992 | Apperson et al. |
| 5,316,009 A | 5/1994 | Yamada |
| 5,369,277 A | 11/1994 | Knodle et al. |
| 5,616,923 A | 4/1997 | Rich et al. |
| 5,693,944 A | 12/1997 | Rich |
| 5,789,660 A | 8/1998 | Kofoed et al. |
| 5,906,204 A | 5/1999 | Beran et al. |
| 6,095,140 A | 8/2000 | Poon et al. |
| 6,099,481 A | 8/2000 | Daniels et al. |
| 6,106,480 A | 8/2000 | Gama De Abreu et al. |
| 6,155,986 A | 12/2000 | Brydon et al. |
| 6,179,784 B1 | 1/2001 | Daniels et al. |
| 6,203,502 B1 | 3/2001 | Hilgendorf et al. |
| 6,227,196 B1 | 5/2001 | Jaffe et al. |
| 6,306,098 B1 | 10/2001 | Orr et al. |
| 6,312,389 B1 | 11/2001 | Kofoed et al. |
| 6,325,978 B1 | 12/2001 | Labuda et al. |
| 6,358,215 B1 | 3/2002 | Ricciardelli |
| 6,390,091 B1 | 5/2002 | Banner et al. |
| 6,394,962 B1 | 5/2002 | Gama De Abreu et al. |
| 6,402,697 B1 | 6/2002 | Calkins et al. |
| 6,408,848 B1 | 6/2002 | Feldman et al. |
| 6,471,658 B1 | 10/2002 | Daniels et al. |

(Continued)

FOREIGN PATENT DOCUMENTS

EP    0728493    8/1996

(Continued)

OTHER PUBLICATIONS

International Search Report, PCT/US2009/055887, dated Feb. 16, 2010.

(Continued)

*Primary Examiner* — Jewel V Thompson

(57) ABSTRACT

A tilt sensor is provided that is generally adapted to detect tilted and non-tilted states of an object associated therewith, which in some cases is a ventilation circuit component. The tilt sensor may correspond to a pneumatically operated tilt sensor that can be used in conjunction with a ventilator to help prevent compromised measurements from certain elements which can be used in a ventilator patient circuit.

18 Claims, 4 Drawing Sheets

U.S. PATENT DOCUMENTS

| | | |
|---|---|---|
| 6,540,689 B1 | 4/2003 | Orr et al. |
| 6,575,164 B1 | 6/2003 | Jaffe et al. |
| 6,616,896 B2 | 9/2003 | Labuda et al. |
| 6,629,934 B2 | 10/2003 | Mault et al. |
| 6,648,831 B2 | 11/2003 | Orr et al. |
| 6,648,832 B2 | 11/2003 | Orr et al. |
| 6,659,962 B2 | 12/2003 | Ricciardelli |
| 6,763,829 B2 | 7/2004 | Jaffe et al. |
| 6,815,211 B1 | 11/2004 | Blazewicz et al. |
| 6,840,906 B2 | 1/2005 | Gama De Abreu et al. |
| 6,908,438 B2 | 6/2005 | Orr et al. |
| 6,945,123 B1 | 9/2005 | Kuehl |
| 6,954,702 B2 | 10/2005 | Pierry et al. |
| 6,955,651 B2 | 10/2005 | Kück et al. |
| 6,990,980 B2 | 1/2006 | Richey, II |
| 7,004,168 B2 | 2/2006 | Mace et al. |
| 7,018,340 B2 | 3/2006 | Jaffe et al. |
| 7,066,176 B2 | 6/2006 | Jaffe et al. |
| 7,074,196 B2 | 7/2006 | Kück et al. |
| 7,135,001 B2 | 11/2006 | Orr et al. |
| 7,183,552 B2 | 2/2007 | Russell |
| 7,291,851 B2 | 11/2007 | DelFavero et al. |
| 7,335,164 B2 | 2/2008 | Mace et al. |
| 7,341,563 B2 | 3/2008 | Rich et al. |
| 7,347,205 B2 | 3/2008 | Levi |
| 7,427,269 B2 | 9/2008 | George et al. |
| 7,432,508 B2 | 10/2008 | Daniels et al. |
| 7,799,231 B2 * | 9/2010 | Irvine .................. 210/695 |
| 2001/0029339 A1 | 10/2001 | Orr et al. |
| 2001/0031928 A1 | 10/2001 | Orr et al. |
| 2002/0103444 A1 | 8/2002 | Ricciardelli et al. |
| 2002/0128566 A1 | 9/2002 | Gama De Abreu et al. |
| 2003/0047188 A1 | 3/2003 | Mace et al. |
| 2003/0191405 A1 | 10/2003 | Rich et al. |
| 2004/0003814 A1 | 1/2004 | Banner et al. |
| 2004/0087867 A1 | 5/2004 | Gama De Abreu et al. |
| 2004/0186391 A1 | 9/2004 | Pierry et al. |
| 2004/0256560 A1 | 12/2004 | Russell |
| 2005/0154320 A1 * | 7/2005 | Froelich et al. ............. 600/486 |
| 2005/0241640 A1 | 11/2005 | Baecke et al. |
| 2005/0279358 A1 | 12/2005 | Richey, II |
| 2005/0285055 A1 | 12/2005 | Delfavero et al. |
| 2006/0009707 A1 | 1/2006 | Daniels et al. |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0145078 A1 | 7/2006 | Russell |
| 2006/0241508 A1 | 10/2006 | Jaffe et al. |
| 2006/0249153 A1 | 11/2006 | DeVries et al. |
| 2006/0253038 A1 | 11/2006 | Kück et al. |
| 2007/0044798 A1 | 3/2007 | Levi |
| 2007/0068518 A1 | 3/2007 | Urias et al. |
| 2007/0107728 A1 | 5/2007 | Ricciardelli et al. |
| 2007/0142716 A1 | 6/2007 | Biondi |
| 2007/0149891 A1 | 6/2007 | George et al. |
| 2007/0157930 A1 | 7/2007 | Soliman et al. |
| 2007/0193579 A1 | 8/2007 | Duquette et al. |
| 2007/0199566 A1 | 8/2007 | Be'eri |
| 2007/0225612 A1 | 9/2007 | Mace |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0282214 A1 | 12/2007 | George et al. |
| 2008/0021339 A1 | 1/2008 | Gabriel et al. |
| 2008/0058667 A1 | 3/2008 | Pierry et al. |
| 2008/0091117 A1 | 4/2008 | Choncholas et al. |
| 2008/0119753 A1 | 5/2008 | Ricciardelli et al. |
| 2008/0119754 A1 | 5/2008 | Hietala |
| 2010/0051026 A1 | 3/2010 | Graboi |
| 2010/0051029 A1 | 3/2010 | Jafari et al. |
| 2011/0146681 A1 | 6/2011 | Jafari et al. |
| 2011/0146683 A1 | 6/2011 | Jafari et al. |

FOREIGN PATENT DOCUMENTS

| | | |
|---|---|---|
| EP | 850652 A2 | 7/1998 |
| EP | 1228779 | 8/2002 |
| EP | 2025358 | 2/2009 |
| EP | 2106818 | 10/2009 |
| JP | 2002136595 | 5/2002 |
| WO | WO9641571 | 12/1996 |
| WO | WO9744636 | 11/1997 |
| WO | WO 98/41268 | 9/1998 |
| WO | WO2007/109177 | 9/2007 |
| WO | WO 2008/042790 | 4/2008 |
| WO | WO 2009/123973 | 10/2009 |

OTHER PUBLICATIONS

International Search Report, PCT/US2009/059102, dated Nov. 30, 2009.

International Search Report, PCT/US200905589, dated Nov. 26, 2009.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Jaffe, Ph.D., "Flow Proximal Measurement with Series 3 Flow Sensors—Technical Issues", Respironics Novametrix, Inc., pp. 1-4, 1012246 SB, Sep. 27, 2002.

PCT International Search Report, Date of Mailing Feb. 1, 2011, Applicant's file reference H-RM-01865WO, International Application No. PCT/US2010/058487, International Filing Date Dec. 1, 2010, 11 pgs.

PCT International Search Report mailed Aug. 2, 2011; International Application No. PCT/US2011/025365, 12 pgs.

International Preliminary Report on Patentability for International (PCT) Patent Application No. PCT/US2009/059102, issued Apr. 5, 2011, 6 pages.

* cited by examiner

TILT SENSOR FOR USE WITH PROXIMAL FLOW SENSING DEVICE

RELATED APPLICATION

This application claims the benefit of U.S. Provisional Application No. 61/101,190 filed Sep. 30, 2008, which application is hereby incorporated herein by reference.

FIELD

The present invention is generally directed to sensors and more particularly to sensors used to detect proper orientation of various objects.

BACKGROUND

Sensors are used in connection with measuring any number of characteristics of objects and the environment around such objects. The complexity of sensors can vary from the most simple sensor, such as a bubble level, to the most complex digital signal processor-based sensors. The cost of a sensor is usually directly proportional to the complexity of the sensor.

The typical objective of using sensors is to detect a certain parameter of interest at the lowest possible cost. While some parameters require the use of complex sensors to be detected accurately, other parameters lend themselves to being detected with less costly sensors. Often times, the key to developing a cost efficient sensor is to leverage features of the object or system being monitored.

Sensors are often used in ventilators. Ventilators are used to provide a breathing gas to a patient who is unable to breathe sufficiently without assistance. Ventilators provide respiratory assistance to patients having a variety of contagious and non-contagious pulmonary disorders, such as pneumonia, ALS or Lou Gehrig's disease, post polio syndrome, head or neck injuries, chronic obstructive pulmonary diseases (asthma, bronchitis, emphysema, etc.), obstructive sleep apnea, congestive heart failure, and neuromuscular paralysis. Flow sensors (i.e., gas flow sensors) are often used in ventilators to ensure that an appropriate amount of gas is flowing to the patient. As can be expected, the types of flow sensors used in ventilators may be relatively costly given the fact that the operation of the potentially life-preserving equipment relies heavily upon knowing that an appropriate amount of gas is flowing to the patient and this, in turn, can depend upon the orientation of the equipment.

SUMMARY

These and other needs are addressed by certain embodiments of the present invention. More specifically, sensors adapted to detect and provide information related to tilted and non-tilted orientations of an object associated therewith are provided. In some embodiments, the sensor generally comprises:

a first flow-through port adapted to receive a first fluid flow; and a flow stopping member, wherein the flow stopping member is moveable between a first position and a second position, wherein, while the flow stopping member is in the first position, flow of the first fluid through the first flow-through port is resisted by the flow stopping member and the orientation of the sensor corresponds to a substantially non-tilted orientation.

In accordance with at least some embodiments of the present invention, the difference between a tilted and non-tilted orientation may be based upon a predetermined angle of tilt threshold. As an example, the threshold for determining whether the sensor is in a tilted or non-tilted orientation may be between about twenty (20) degrees and about forty (40) degrees of tilt away from level. More specifically, in one embodiment if the sensor is initially in a non-tilted orientation such that the flow stopping member is inhibiting flow through the tilt sensor and then the sensor is rotated 40 degrees or more away from level, then the flow stopping member may move away from blocking the fluid flow and sensor is considered to be in a tilted orientation. Then, in one embodiment after the sensor is in the tilted orientation, it may not go back to a non-tilted orientation until the tilt sensor is rotated to less than 20 degrees away from level.

It is one aspect of the present invention to provide a mechanism for detecting when a sensor and an object associated with the sensor is in a tilted or non-tilted state (e.g., in response to detecting whether flow through the tilt sensor has been stopped or not). Embodiments of the present invention may be particularly useful in detecting tilt in any number of applications. As one example, a tilt sensor may be mechanically rigidly connected to and thereby associated with a ventilator or at least a portion of a ventilator circuit (e.g., a patient wye or a proximal flow sensor connected to a patient wye). It is preferable in certain ventilator applications to ensure that the primary flow paths through a portion of the ventilator such as a proximal flow sensor are substantially level so that patient secretions, mucus, and the like do not obstruct the tubing used to measure proximal flow. If secretions were allowed to collect in one or both such hoses, then operations of the ventilator would be compromised. Thus, it is desirable to maintain a preferred orientation of portions of the ventilator to prevent this unwanted buildup. A ventilator equipped with a tilt sensor in accordance with at least some embodiments of the present invention will be capable of avoiding this unwanted buildup.

There are a number of different ways to detect tilt of an object. At least some embodiments of the present invention provide a pneumatically operated tilt sensor. Depending upon the desired orientation of a particular object, a tilt sensor may be located at any position relative to the object to which it is attached (i.e., the object which is having its tilt measured/monitored). In one embodiment, a tilt sensor may be provided that defines a non-tilting state when the tilt sensor is in a substantially vertical orientation. If such a tilt sensor is employed, then the tilt sensor may be positioned in a substantially orthogonal orientation relative to any device, conduit, or object that is desired to have a level or horizontal orientation. Likewise, if the same vertically-biased tilt sensor is employed on an object that is designed to have a vertical orientation, then the tilt sensor may be oriented substantially parallel to the object.

The present invention further provides methods for detecting whether an object is tilted or not. In accordance with at least some embodiments of the present invention, a method of determining the orientation of an object is provided that generally comprises:

receiving a fluid flow in a primary flow path;

detecting at least one of a decrease in the fluid flow through the primary flow path and an increase in pressure in the primary flow path; and in response to the detecting step, determining that the tilt sensor comprises a tilted or a not tilted orientation.

Additional features and advantages of embodiments of the present invention will become more readily apparent from the following description, particularly when taken together with the accompanying drawings.

DETAILED DESCRIPTION

Figure 1:
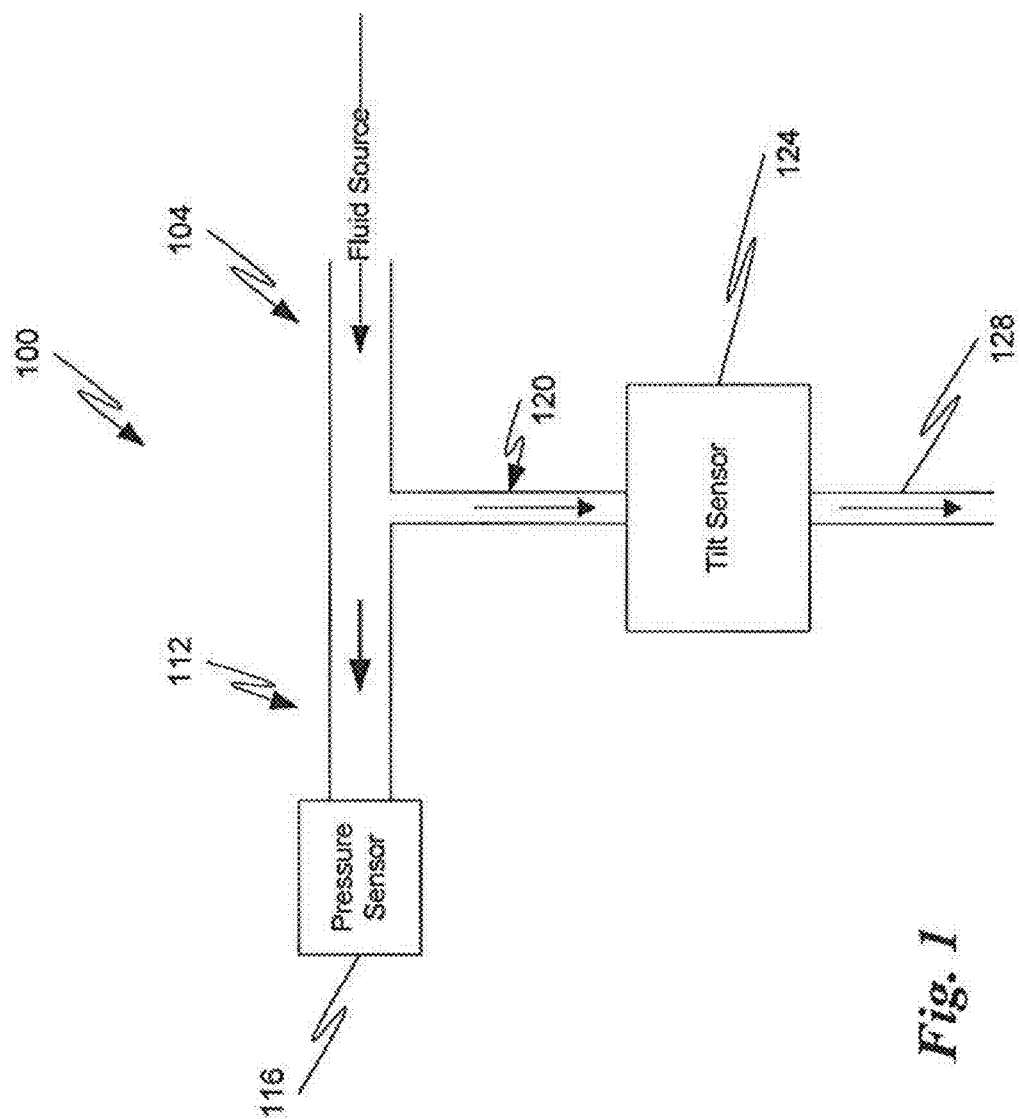
FIG. 1 is a block diagram depicting a tilt sensor in accordance with at least some embodiments of the present invention.

With reference now to FIG. 1, an exemplary tilt sensor circuit will be described in accordance with at least some embodiments of the present invention. While certain embodiments of the present invention will be discussed in connection with measuring and monitoring the orientation of a component or collection of components in a ventilator system, one skilled in the art will appreciate that embodiments of the present invention may be equally useful in measuring and monitoring the orientation of any type of object or collection of objects, including other medical devices.

The tilt-sensing system 100 may be adapted to attach or be otherwise rigidly associated with a ventilator system used to assist breathing functions of a patient. The ventilator system may include a ventilator (not shown) connected to a fluidic circuit that is separate from the patient circuit.

In accordance with at least one embodiment of the present invention, a pressure sensor 116 may be provided on an output branch 112 of the tilt-sensing system 100. The tilt-sensing system 100 may also include an input branch 104 having a fluid (e.g., air, gas, etc.) source and a tilt sensor input branch 120. The pressure sensor 116 may be operable to detect fluidic pressure within the output branch 112 and report some value that is an indication of the detected fluid flow through the tilt sensor 124 or pressure in the circuit.

In accordance with at least some embodiments of the present invention, the sensor 116 may be a differential pressure sensor, a collection of individual pressure sensors located at various points along the circuit, or any other type of pressure measuring device.

In some embodiments, the pressure sensor 116 is remotely connected to the tilt sensor 124 via a flexible, possibly thin, tube. In some embodiments the tilt sensor 124 may be rigidly attached to an object having it's tilt monitored. In some embodiments the pressure sensor 116 may be rigidly attached to an object having it's tilt monitored while in other embodiments the pressure sensor 116 may not be connected to the object at all.

In accordance with at least some embodiments of the present invention, the tilt sensor 124 may be associated with (e.g., rigidly attached to) a component of a ventilator system by being physically connected to the component of the ventilator system. For example, if the tilt sensor 124 is employed to monitor the orientation of a proximal flow sensor (not shown), then the tilt sensor 124 may be connected to the pressure sensor 116 possibly through long, flexible tubing 120 such that alterations in the orientation of the proximal flow sensor (not shown) are detected by the tilt sensor 124 (e.g., because the orientation of the tilt sensor 124 is altered). Tilt sensor 124 may be coupled to the ventilation component using a wide variety of coupling devices or methods, including snap-together connectors, straps, cables, adhesives, and the like. In other embodiments, the tilt sensor 124 may be an integral part of the pressure sensor 116.

Alternatively, fluid flow to the tilt sensor 124 may be provided by an external source and not from the patient circuit (e.g., from a separate fluid source).

As can be seen in FIG. 1, in one exemplary system configuration, the input port 120 of the tilt sensor 124 may be in communication with a primary fluid flow path in the tilt-sensing system 100. The tilt sensor 124 is adapted to detect whether a component(s) of an associated device (e.g., proximal flow sensor) is in a tilted or non-tilted state. The tilt sensor 124 is employed to give an early warning that the orientation of a component in the ventilator system to reduce the possibility that secretions might start to reduce the accuracy of patient airway flow measurements. Thus, a properly designed tilt sensor 124 can be used to alert users and/or technicians that ventilation flow measurements may be compromised due to the improper orientation of the tilt sensor 124. It is useful to obtain this early detection to help prevent any diagnosis based on inaccurate ventilation flow measurements.

As can be appreciated, many types of tilt sensor may be used in connection with measuring the orientation of components in a ventilator system. In accordance with at least one exemplary embodiment of the present invention, the tilt sensor 124 may be pneumatically operated and adapted to work in cooperation with the fluid flowing through the primary flow path. Other types of tilt sensor may also be useful to use alone or in combination with a pneumatically operated tilt sensor 124 in certain embodiments of the present invention.

Figure 4:
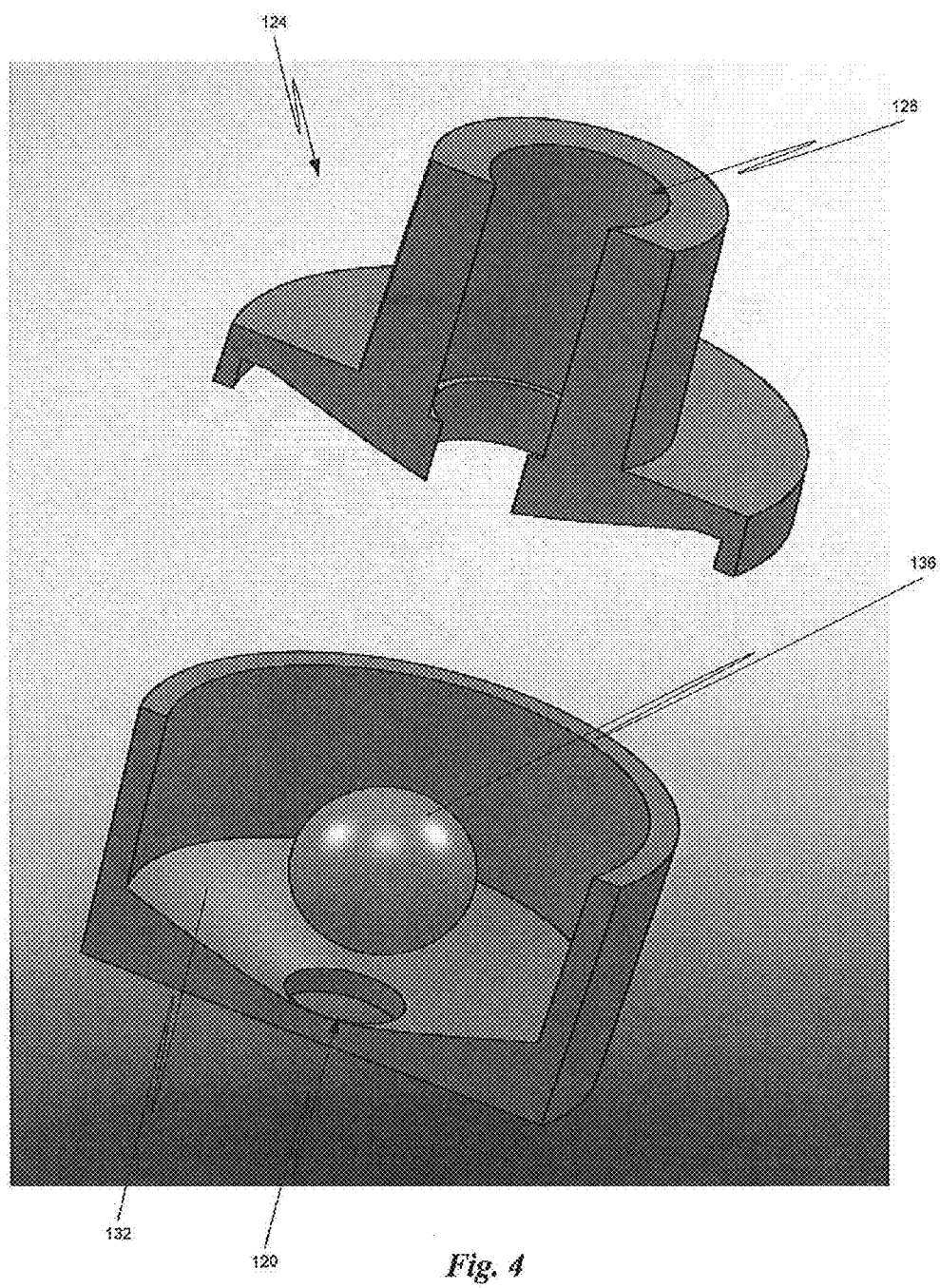
FIG. 4 is a cross-sectional perspective view of an exemplary tilt sensor in accordance with at least some embodiments of the present invention.

One exemplary embodiment of the tilt sensor 124 is depicted in FIG. 4. In FIG. 4 a tilt sensor 124 is depicted that includes an inclined surface 132 that transitions into an orifice or tilt sensor output 120. The tilt sensor 124 may also include a flow stopping member 136 that is operable to engage with and cover the orifice 120 when the tilt sensor 124 is in a preferred orientation (i.e., a non-tilt orientation in this case).

The inclined surface 132 may be designed such that the weight of the flow stopping member 136 brings the flow stopping member 136 over the orifice 120. The flow stopping member may have a slightly larger external dimension than the dimensions of the orifice 120. As one example, the flow stopping member 136 may comprise a spherical element, such as a ball. Thus, when the flow stopping member 136 is positioned over the orifice 120, fluid is substantially inhibited from flowing through the orifice 120. This substantially stops all fluid flow in the tilt sensor system 100. This particular state can be detected either by the sensor 116 detecting a higher pressure than would be detected when the flow stopping element 136 is not positioned over the orifice 120.

In another embodiment, if the flow stopping member 136 is blocking the orifice 120, then a pressure or flow sensor disposed within or in communication with the tilt sensor 124 can detect a non-tilted orientation of tilt sensor 124 and communicate this information to the ventilator system. Alternatively, if flow stopping member 136 is not blocking the orifice 120 (e.g., when tilt sensor 124 is tilted), then the pressure and/or flow sensor disposed within or in communication with the tilt sensor 124 detects the tilted orientation and communicates this data to the ventilator system. Such embodiments may be particularly useful, for example, when it is desired to know the orientation of a component of a ventilation circuit.

As can be appreciated by one skilled in the art, the flow stopping member 136 and/or orifice 120 and/or inclined surface 132 and/or housing 124 may assume any number of different configurations. Examples of some alternative configurations for the flow stopping member 136 include, without limitation, a washer, a donut, a ring, a cylinder, or any other object that can roll down the inclined surface 132 under its own weight. The orifice 120 may be designed to receive and be blocked by any type of flow stopping member 136 that is employed. For instance, if the flow stopping member 136 is designed like a ring, then the orifice 120 may be a slot whose length is less than the diameter of the ring and whose width is less than or equal to the thickness of the ring.

In embodiments where a spherical flow stopping member 136 is employed, the inclined surfaces 124 of the tilt sensor 124 may comprise a conical shape. Thus, the tilt sensor 124 may be adapted to detect tilt about any plane whereas a tilt sensor 124 with a ring or donut flow stopping member 136 may only be enabled to detect tilt about one plane.

In some embodiments, the tilt sensor 124 is designed to cause the flow stopping member 136 to wander out of the orifice 120 after the tilt sensor 124 has been tilted a predetermined angle. This predetermined angle may be determined by the geometry of the stopping member 136, the weight of the stopping member 136, the type of material used to create the stopping member 136, the geometry and texture of the inclined surface 132, and the amount and type of fluid flowing in the system 104. With a proper design of the stopping member 136, orifice 120, and inclined surface 132 it can be determined what angle of tilt will cause fluid to flow through the orifice 120. The angle of the inclined surface 132 will, in part, also help determine when the flow stopping member 136 will begin to roll back into the orifice (i.e., after it is out of the orifice 120). In accordance with at least some embodiments of the present invention, the inclined surfaces 132 of the tilt sensor 124 may comprise a number of different surfaces having a number of different angles of inclination. As an example, the angle of inclination (i.e., the angle between the surface of the inclined surface 132 and a plane which is either orthogonal to the path of fluid flow through the orifice 120 or parallel to the base of the tilt sensor 124) may be as large as about thirty (30) degrees. In some embodiments, the angle of inclination of the inclined surface 132 may be between about ten (10) degrees and about fifteen (15) degrees. Based on the properties of the flow stopping member 136 and inclined surface 132, these angles of inclination may correspond to operational tilt angles between ten (10) degrees and forty (40) degrees. An operational tilt angle differs from the angle of inclination of the inclined surface 132 in that the operational tilt angle is the angle at which the tilt sensor 124 needs to be tilted to cause the state of the tilt sensor 124 to change from tilted to non-tilted or vice versa, whereas the angle of inclination corresponds to the physical angle at which the inclined surface 132 is oriented.

The inclined surfaces 124 may be designed such that precise control over when the orifice 120 is blocked or not can be obtained and the angle of inclination causing the flow stopping member 136 to move out of the orifice 120 may be different from the angle of inclination causing the flow stopping member 136 to move back over the orifice 120.

As an example, a tilt of forty (40) degrees off vertical may cause the flow stopping member 136 to move away from the orifice 120 whereas a tilt of twenty (20) degrees is required to cause the flow stopping member 136 to move back into the orifice 120 after it is out of the orifice 120. This may be facilitated by employing multiple inclined surfaces 124 each having different angles of inclination. In other words, the tilt sensor 124 can be designed to have two angles where the tilt activates and deactivates. The dual angles of inclination can help create an anti-chatter mechanism that allows the tilt sensor 124 to tolerate a certain amount of patient movement without switching between a tilted state and non-tilted state.

As can be appreciated by one skilled in the art, although a pressure sensor 116 is shown being connected to output branch 112 of the tilt-sensing system 110, a flow sensor may be used as an alternative to the pressure sensor 116. Furthermore, a flow sensor or series of flow sensors may be used in combination with a pressure sensor 116 or series of pressure sensors without departing from the scope of the present invention.

Figure 2:
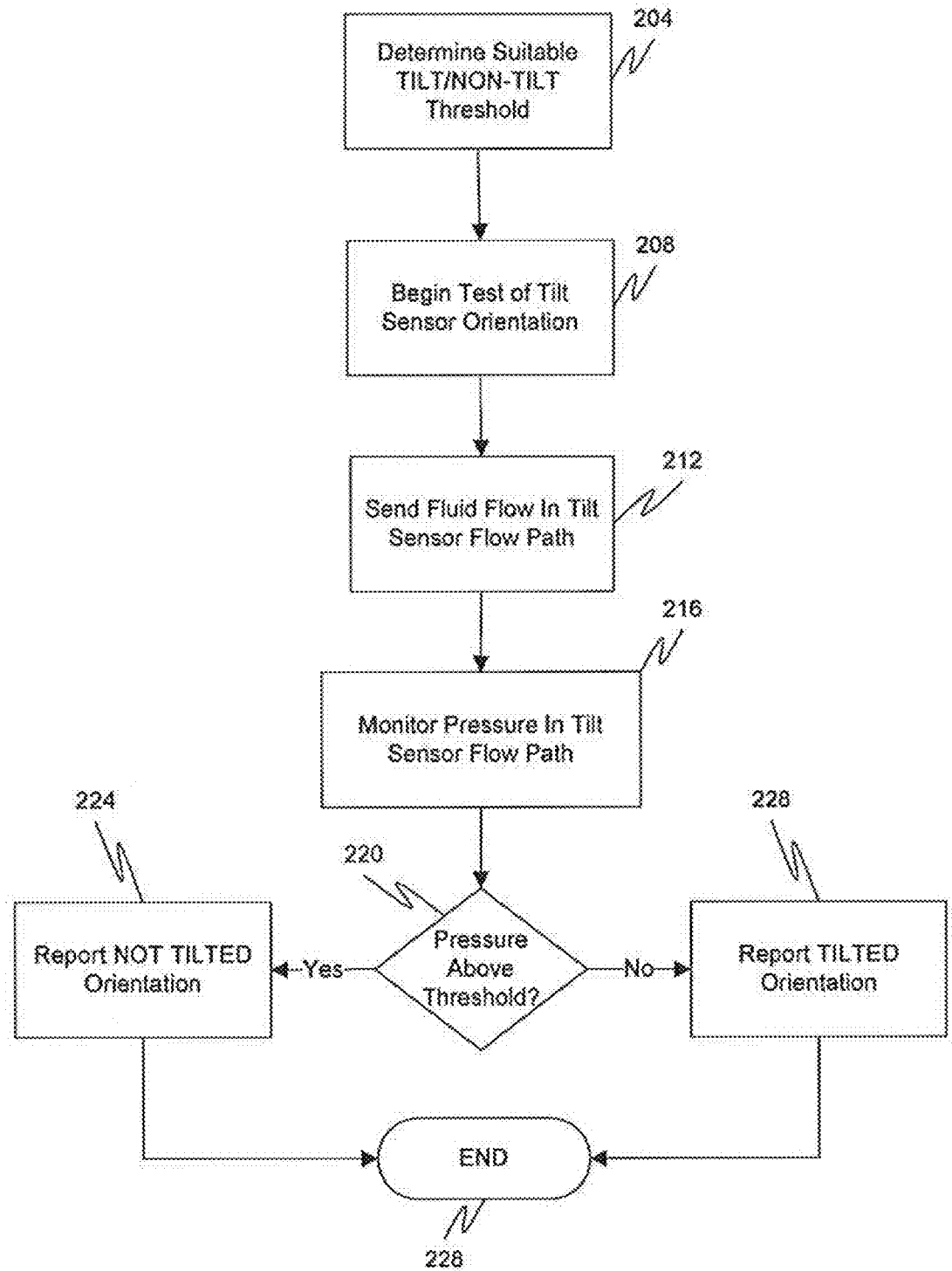
FIG. 2 is a flow chart depicting a periodic tilt sensing method in accordance with at least some embodiments of the present invention.

With reference to FIG. 2, a periodic tilt detection method will be described in accordance with at least some embodiments of the present invention. The method begins by determining a suitable tilt/non-tilt threshold (step 204). This threshold is defined by the properties of the tilt sensor 124 and/or properties used to actuate the tilt sensor 124. As noted above, the threshold used to determine whether the tilt sensor 124 is in a tilted orientation may include a predetermined flow and/or pressure measurement that is measured by the pressure sensor 116.

After the tilt threshold has been determined, the method continues when it becomes time to test the orientation of the tilt sensor 124 (step 208) at which time fluid is flowed toward the tilt sensor 124 in the tilt sensor flow path 120 (step 212). In accordance with at least some embodiments of the present invention, the fluid may include, but is not limited to, wall air, gas from a compressor, or gas from a tank. The pressure sensor 116 monitors the pressure in the tilt sensor flow path 120 and the primary flow path (step 216).

The measured pressure is then compared to the predetermined tilt threshold (step 220) to determine whether the tilt sensor 124 is in a tilted or non-tilted state. Since the tilt sensor 124 is also associated with some other component or collection of components (e.g., a ventilator system component such as a proximal flow sensor), the orientation of that component can be inferred by determining the orientation of the tilt sensor 124.

In the event that the measured pressure is above the predetermined tilt threshold, then a non-tilted orientation is reported for the tilt sensor 124 (step 224). Alternatively, if the measured pressure is below the tilt threshold, then a tilted orientation is reported for the tilt sensor 124 (step 228). Once the tilt orientation has been reported the method ends (step 228) until the next time a tilt test is performed.

Figure 3:
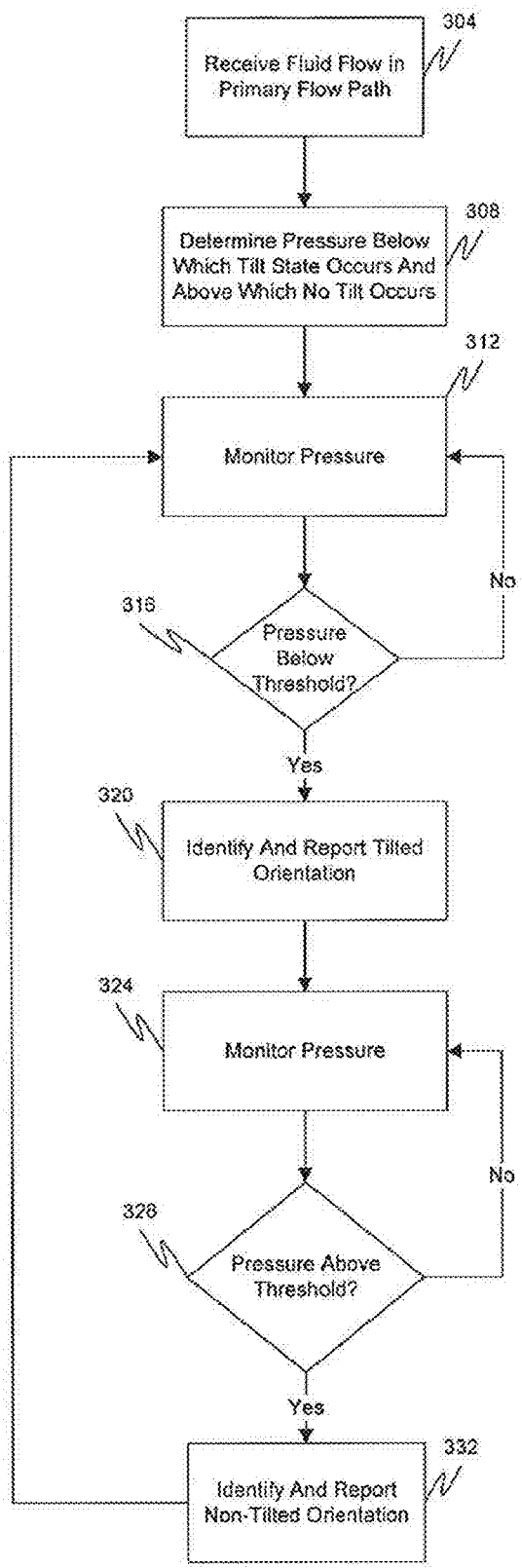
FIG. 3 is a flow chart depicting a continuous tilt sensing method in accordance with at least some embodiments of the present invention.

Referring now to FIG. 3, an exemplary continuous tilt detection method will be described in accordance with at least some embodiments of the present invention. The method includes receiving fluid flow in a primary fluid flow path (step 304). Thereafter, the method determines the pressure threshold for identifying a reduced pressure state in the primary flow path (i.e., a tilted state) and a normal pressure state in the primary flow path (i.e., a non-tilted state) (step 308). In other words, a tilt state pressure threshold is determined for both a tilted state and a non-tilted state. The threshold or trigger identified in step 308 may vary depending upon the type of pressure sensor being used in the primary flow path as well as the location of the tilt sensor 124.

The method continues with the pressure sensor 116 monitoring the pressure of the fluid flow in the primary fluid flow path for a reduced pressure (step 312) until a reduced pressure is detected (step 316). Once a reduced pressure is detected (i.e., the pressure measured at the pressure sensor 116 has fallen below a predetermined tilt state pressure threshold), the method includes the tilt sensor 124 reporting a tilted orientation of the tilt sensor 124 (step 320). This may be reported in a buzzer, light, or other type of audible/visible indication to a user. Alternatively, the tilt may be reported to a remote location and may also be stored in a tilt log.

After a tilt condition has been detected, in some embodiments the method includes monitoring the pressure of the primary flow path for an increase in pressure (step 324) until a return to normal pressure conditions has been detected (i.e., the pressure measured at the pressure sensor 116 has risen above the predetermined tilt state pressure threshold)(step 328). In accordance with at least one embodiment of the present invention, this trigger may correspond to detecting an increase in the pressure in the primary flow path 108, 112. Once this trigger has been detected, the method includes identifying and reporting the non-tilted orientation of the tilt sensor (step 332). Then the method returns to step 312.

Referring again to FIG. 4, in some embodiments the tilt sensor 124 comprises two separate components that are adapted to cooperate with one another and form a cavity, which may or may not be air-tight, for the flow stopping member 136. The orifice 120 of the tilt sensor 124 which is adapted to be blocked by the flow stopping member 136 in a non-tilted orientation may have the inclined surface 132 that biases the flow stopping member 136 toward the orifice 120. The opposite orifice of the tilt sensor 124 (i.e., the orifice of the upper component depicted in FIG. 4) may also comprise tilted surfaces that are designed to deter the flow stopping member 136 from blocking the opposite orifice. The deterrent tilted surfaces are useful to prevent the tilt sensor 124 from providing erroneous pressure data in an upside-down configuration. More specifically, if the tilt sensor 124 were completely upside-down, the deterrent tilted surfaces may prevent the flow stopping member 136 from stopping the flow of fluid through the tilt sensor 124, thereby preventing a false non-tilted orientation reading.

In accordance with at least some alternative embodiments of the present invention, an "ON-OFF" switch for the tilt sensor 124 may also be provided. It may be advantageous to have some means of sampling the state of the tilt sensor 124 by turning the gas ON, measuring the pressure, then turning the gas OFF. Because if it were ON continuously the gas pressure would keep the flow stopping member 136 in its seat and not let it wander away during a TILT condition. However, if the flow stopping member 136 were heavy enough, and the gas pressure were low enough, in that case it could work without a means for interrupting the gas flow.

Other applications where such a tilt sensor 124 may be useful is in explosive environments, where electrically operated tilt sensors run the risk of malfunction and creating a spark, causing an explosion, or any application where tilt sensing is needed in a sensitive area, such as near a patient being ventilated, without the use of electrical wiring directly to the tilt sensor.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A sensor adapted to detect and provide information related to tilted and non-tilted orientations, the sensor comprising:

a first flow-through port adapted to receive a first fluid flow; and a flow stopping member, wherein the flow stopping member is moveable between a first position and a second position, wherein, while the flow stopping member is in the first position, flow of the first fluid through the first flow-through port is measurably inhibited by the flow stopping member and an orientation of the sensor corresponds to a substantially non-tilted orientation.

2. The sensor of claim 1, wherein, while the flow stopping member is in the second position, a measurable amount of the first fluid flows through the first flow-through port and the orientation of the sensor corresponds to a tilted orientation.

3. The sensor of claim 2, wherein a first input port is connected to a primary fluid flow path, and wherein flow of the first fluid through the first flow-through port is detected by detecting at least one of a decreased pressure and increased flow rate in the primary fluid flow path.

4. The sensor of claim 1, wherein the flow stopping member comprises a plug that is movable by accelerative forces and wherein the first flow-through port comprises an orifice and at least one inclined surface that is adapted to draw the moveable plug over the orifice and substantially inhibit flow of the first fluid through the orifice when the sensor is in the non-tilted orientation.

5. The sensor of claim 4, wherein the at least one inclined surface of the first flow-through port comprises a conical interface and the moveable plug comprises a spherical object adapted to sit within the conical interface and cover the orifice only when the first flow-through port is oriented substantially vertically.

6. The sensor of claim 4, wherein the at least one inclined surface comprises a first inclined surface and a second inclined surface, wherein the first inclined surface comprises a first angle of inclination and the second inclined surface comprises a second angle of inclination, and wherein the first and second angles of inclination are different.

7. The sensor of claim 1, wherein the non-tilted orientation comprises a vertical orientation of the first flow-through port within a tolerance of about plus or minus twenty degrees deviation from vertical.

8. The sensor of claim 1, wherein the first fluid comprises at least one of wall air, gas from a compressor, and gas from a tank.

9. A method of determining an orientation of an object, comprising:

receiving a fluid flow in a primary flow path;

detecting at least one of an increase in the fluid flow through the primary flow path and a decrease in pressure in the primary flow path;

in response to the detecting step, determining that the primary flow path comprises a tilted orientation, wherein the primary flow path comprises a sensor flow path in fluidic communication therewith and wherein the fluid flow through the sensor flow path occurs when the primary flow path comprises the tilted orientation; and a flow stopping member that is operable to inhibit the fluid flow through the sensor flow path when the primary flow path comprises a non-tilted orientation, wherein the flow stopping member comprises a plug that is movable by gravitational forces and wherein the sensor flow path comprises an orifice and at least one inclined surface that is adapted to draw the moveable plug over the orifice and inhibit flow of the fluid through the orifice when the sensor flow path is in a non-tilted orientation.

10. The method of claim 9, wherein the at least one inclined surface comprises a conical interface and the moveable plug comprises a spherical object adapted to sit within the conical interface and cover the orifice only when the sensor flow path is oriented substantially vertically.

11. The method of claim 10, wherein the at least one inclined surface comprises a first inclined surface and a second inclined surface, wherein the first inclined surface comprises a first angle of inclination and the second inclined surface comprises a second angle of inclination, and wherein the first and second angles of inclination are different.

12. The method of claim 9, wherein the non-tilted orientation comprises a vertical orientation of the sensor flow path within a tolerance of about plus or minus twenty degrees deviation from vertical.

13. A non-transitory computer readable medium comprising processor executable instructions that, when executed, perform the detecting and determining steps of claim 9.

14. A comparator operable to perform the detecting and determining steps of claim 9.

15. A system, comprising:
a primary fluid flow path;
a tilt sensor comprising a fluid flow path and a flow stopping member adapted to inhibit fluid from flowing through the tilt sensor fluid flow path in a first position and further adapted to allow fluid flow through the tilt sensor fluid flow path in a second position; and
a pressure sensor operable to detect that the flow stopping member is in the second position by detecting a decrease in fluidic pressure in the primary fluid flow path.

16. The system of claim 15, wherein, while the flow stopping member is in the first position, flow of the fluid through a first flow-through port is substantially inhibited by the flow stopping member and an orientation of the sensor corresponds to a non-tilted orientation.

17. The system of claim 15, wherein, while the flow stopping member is in the second position, an orientation of the sensor corresponds to a tilted orientation.

18. The system of claim 16, wherein the non-tilted orientation comprises a vertical orientation of the tilt sensor within a tolerance of about plus or minus twenty degrees deviation from vertical.

* * * * *